United States Patent [19]
Alo et al.

[11] Patent Number: 6,104,957
[45] Date of Patent: *Aug. 15, 2000

[54] EPIDURAL NERVE ROOT STIMULATION WITH LEAD PLACEMENT METHOD

[76] Inventors: Kenneth M. Alo, 4512 Teas, Bellaire, Tex. 77401; Claudio A. Feler, 350 Sweetbriar Rd., Memphis, Tenn. 38120

[ * ] Notice: This patent issued on a continued prosecution application filed under 37 CFR 1.53(d), and is subject to the twenty year patent term provisions of 35 U.S.C. 154(a)(2).
This patent is subject to a terminal disclaimer.

[21] Appl. No.: 09/138,065

[22] Filed: Aug. 21, 1998

[51] Int. Cl.[7] ........................................ A61N 1/05
[52] U.S. Cl. ..................... 607/46; 128/898; 128/899; 607/117
[58] Field of Search .................. 128/899, 898; 607/2, 46, 117, 118; 600/26

[56] References Cited

U.S. PATENT DOCUMENTS

| | | | |
|---|---|---|---|
| 4,549,556 | 10/1985 | Tarjan et al. | 607/117 |
| 4,607,639 | 8/1986 | Tanagho et al. | 128/419 E |
| 4,703,755 | 11/1987 | Tanagho et al. | 128/419 R |
| 4,739,764 | 4/1988 | Lue et al. | 128/419 R |
| 4,940,065 | 7/1990 | Tanagho et al. | 128/784 |
| 5,255,691 | 10/1993 | Otten | 607/117 |
| 5,370,670 | 12/1994 | Chancellor | 607/40 |
| 5,591,724 | 1/1997 | Morales et al. | 514/54 |
| 5,672,517 | 9/1997 | Domingue | 436/518 |
| 5,698,549 | 12/1997 | Steers et al. | 514/211 |
| 5,733,322 | 3/1998 | Starkebaum | 607/117 |
| 5,752,978 | 5/1998 | Chancellor | 607/40 |

OTHER PUBLICATIONS

Barolat, "Percutaneous retroperitoneal stimulation of the sacral plexus", *Stereotact Funct Neurosurg*, 56(4):250–7 (1991).

*Primary Examiner*—Kennedy J. Schaetzle
*Attorney, Agent, or Firm*—Sidley & Austin

[57] ABSTRACT

A method of managing chronic pain and/or symptoms of motor dysfunction produced by a variety of disorders or conditions. The method includes techniques for positioning one or more stimulation leads so as to enable delivery of electrical energy to epidural spinal nervous tissue, spinal ganglia, nerve plexi, or peripheral nerves using superior-to-inferior and/or trans-spinal advancement relative to a vertebral column and stimulating selected spinal nervous tissue.

42 Claims, 6 Drawing Sheets

EPIDURAL NERVE ROOT STIMULATION WITH LEAD PLACEMENT METHOD

FIELD OF THE INVENTION

The present invention relates to a method of managing human chronic pain and/or controlling symptoms of motor dysfunction, and in particular, to a method of applying electrical energy through electrical stimulation electrodes particularly positioned along certain spinal nervous tissue to inhibit or interfere with the transmission of signals along spinal neural pathways 10 related to chronic pain and/or motor dysfunction.

BACKGROUND OF THE INVENTION

Application of specific electrical energy to the spinal cord for the purpose of managing pain has been actively practiced since the 1960s. While a precise understanding of the interaction between the applied electrical energy and the nervous tissue is not fully appreciated, it is known that application of an electrical field to spinal nervous tissue can effectively mask certain types of pain transmitted from regions of the body associated with the stimulated tissue. More specifically, applying particularized electrical pulses to the spinal cord associated with regions of the body afflicted with chronic pain can induce paresthesia, or a subjective sensation of numbness or tingling, in the afflicted bodily regions. This paresthesia can effectively inhibit the transmission of non-acute pain sensations to the brain.

Electrical energy, similar to that used to inhibit pain perception, may also be used to manage the symptoms of various motor disorders, for example, tremor, dystonia, spasticity, and the like. Motor spinal nervous tissue, or nervous tissue from ventral nerve roots, transmits muscle/motor control signals. Sensory spinal nervous tissue, or nervous tissue from dorsal nerve roots, transmit pain signals. Corresponding dorsal and ventral nerve roots depart the spinal cord "separately"; however, immediately thereafter, the nervous tissue of the dorsal and ventral nerve roots are mixed, or intertwined. Accordingly, electrical stimulation intended to manage/control one condition (for example, pain) often results in the inadvertent interference with nerve transmission pathways in adjacent nervous tissue (for example, motor nerves).

Electrical energy is commonly delivered through electrodes positioned external to the dura layer surrounding a spinal cord. The electrodes are carried by two primary vehicles: the percutaneous lead and the laminotomy lead. As the present invention primarily concerns the placement of percutaneous leads (i.e., any lead which may be positioned within an epidural space using an external insertion needle), a further discussion or description of laminotomy leads (i.e., leads which require surgical removal of vertebral material to allow access to an epidural space) will not be provided here.

Percutaneous leads commonly have two or more electrodes and are positioned within an epidural space through the use of an insertion, or Touhy-like, needle. An example of an eight-electrode percutaneous lead is an OCTRODE® lead manufactured by Advanced Neuromodulation Systems, Inc. of Allen, Tex.

Figure 1A:
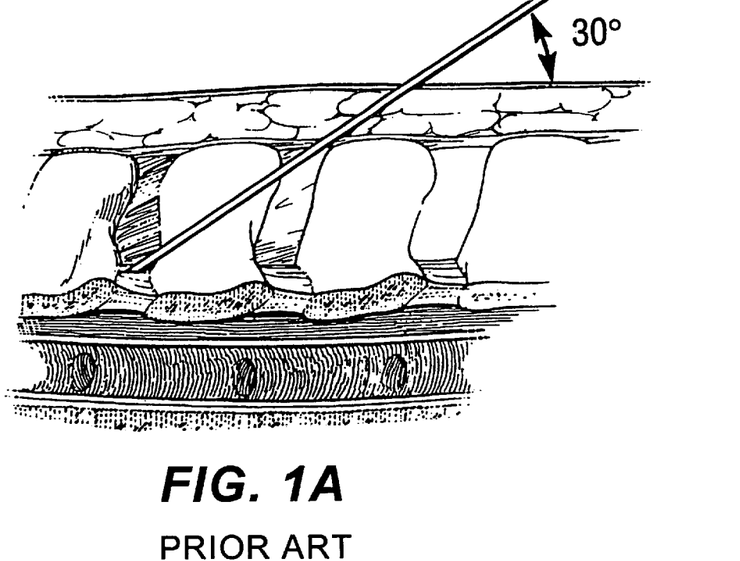
FIG. 1a is a partial, sectional side view illustrating a conventional percutaneous stimulation lead insertion technique in a rostral, or superior, direction relative to a dorsal column.
Figure 1B:
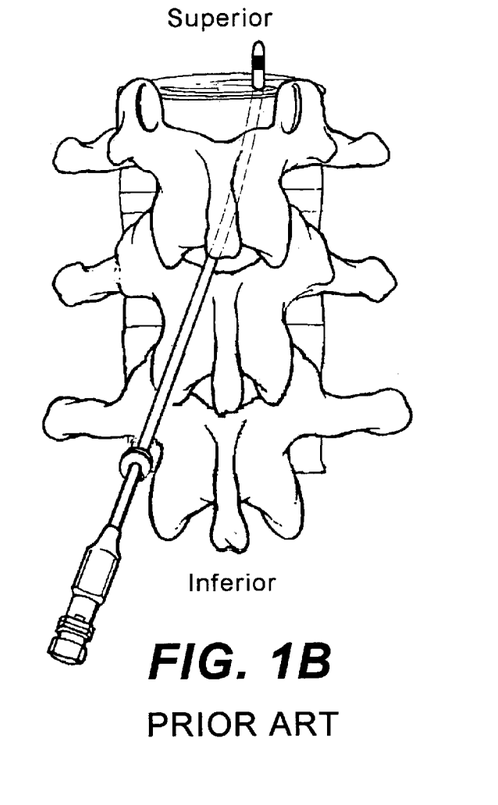

Operationally, an insertion needle is passed through the skin, between the desired vertebrae, and into an epidural space which is defined by a dural layer in combination with the surrounding vertebrae. The stimulation lead is then fed through the bore of the insertion needle and into the epidural space. Conventionally, the needle is inserted at an inferior vertebral position, for example, between vertebrae L1 and L2 (L1/L2)(see FIGS. 1a and 1b), and the stimulation lead is advanced in a superior direction until the electrodes of the stimulation lead are positioned at a desired location within the epidural space, for example, at T10. In a lateral position, percutaneous leads are typically positioned about a physiological midline.

As an example of application, the above methodology is commonly used for the management of sympathetically maintained pain (SMP). It is generally believed that due to the sympathetic nature of SMP, stimulation leads positioned about a physiological midline provide sufficient electrical energy to interrupt the transmission of SMP signals. This may be because sympathetically maintained-type pain requires less nervous fiber selection and/or is less susceptible to interference by interpositioned cerebrospinal fluid.

Figure 2A:
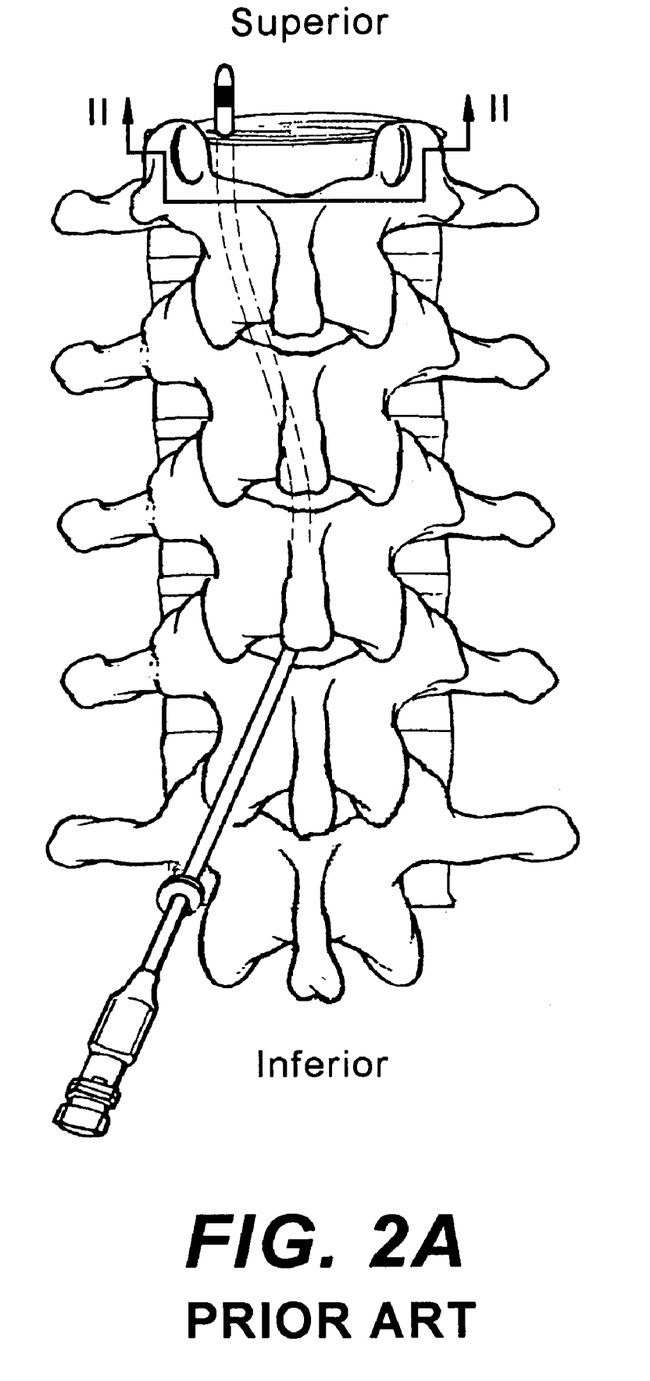
FIG. 2a is a partial, plan view illustrating a conventional percutaneous stimulation lead placement technique to allow stimulation of spinal nerve roots.

The above-described conventional technique is used less often for the management of sympathetically independent pain (SIP). SIP is somatic in nature or a mixture of somatic and sympathetic. While it is recognized that SIP could potentially be managed by conventional implantation methods, there currently exists an inability to consistently achieve either a required level of nervous fiber selection or adequate stimulation through interpositioned cerebrospinal fluid at the stimulation site. Consequently, to manage SIP, electrical energy is commonly delivered to the spinal nerve roots corresponding to the pain-afflicted dermatomes. Using conventional implantation methods, electrical energy can only be applied to nerve roots by placing a percutaneous lead in lateral extremes of the epidural space, or in the epidural "gutters" (see FIGS. 2a and 2b). Of note, however, a percutaneous lead inserted at an inferior location and advanced in a superior direction cannot reach the epidural gutters above C2/C3 of a vertebral column.

Figure 2B:
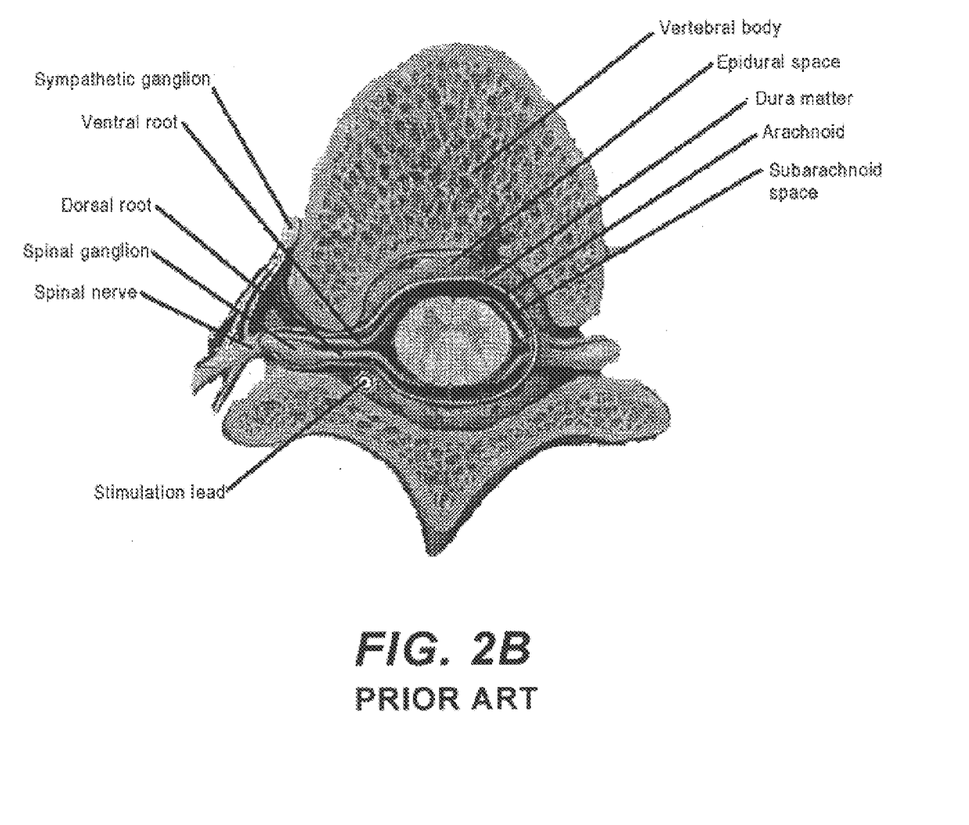

As seen in FIG. 2b, positioning a stimulation lead in this manner results in the electrode portion of the stimulation lead spanning a plurality of nerve roots. To stimulate the correct nerve root(s), it is critical that the applied electrical energy be properly defined. An improperly defined electric field may not only be ineffective in controlling/managing the desired condition(s) but may also inadvertently interfere with the proper neural pathways of adjacent spinal nervous tissue.

An applied electrical field is defined by the polarity of each electrode of the stimulation lead. Conventionally, each electrode is set as an anode (+), cathode (−), or neutral (off). As may be understood, for a four electrode percutaneous lead there exists approximately 50 electrode combinations. For an eight electrode percutaneous lead, the number of possible electrode combinations grows to approximately 6050.

Utilizing conventional implantation techniques, a user must rely solely upon effectively programming the electrodes of a multiple electrode percutaneous catheter to define an electric field for "selection" of spinal nervous tissue to either inhibit the transmission of pain signals to the brain or control the symptoms of a motor/muscular disorder. Unfortunately, the time required to identify/define an optimum electric field may be prohibitive.

As an alternative to spinal cord stimulation, electrical energy may be delivered to selected peripheral nerves using a peripheral nerve stimulation system. Peripheral nerve stimulation involves administration of electrical energy to a localized group of peripheral nerves through placement of one or more leads at the peripheral nerve site. Unfortunately, if a patient's pain is widespread, a patient may require a plurality of stimulation leads to be implanted. The surgical procedure necessary for stimulation lead implantation is significant and can be quite painful. Additionally, because peripheral stimulation leads are implanted in "active" areas of the body (e.g., arms and legs), the leads typically lack long-term placement stability. Lead movement, or lead migration, can affect the quality of pain relief. Further, significant lead movement that undermines the intended stimulation effect may require additional corrective surgeries to reposition the stimulation leads.

Accordingly, a need exists for a technique that enables the effective placement of multiple electrode stimulation leads which allows "selection" of desired spinal nervous tissue to manage chronic pain and/or symptoms of motor dysfunction.

SUMMARY OF THE INVENTION

The present invention is drawn to a method of managing chronic pain and/or controlling motor dysfunction symptoms through application of electrical energy to selected spinal nervous tissue. The stimulation system includes a signal generator and at least one stimulation lead having an electrode portion and a connector portion, where the connector portion may be electrically coupled to the signal generator. The stimulation lead is positioned so that the electrode portion of the stimulation lead lies in a plane substantially parallel to selected spinal nervous tissue, the selected nerve tissue including at least one of: epidural spinal nervous tissue, spinal ganglion, neural plexus, and peripheral nerves. Following coupling the stimulation lead to the signal generator, electrical energy is delivered from the signal generator to the electrode portion of the stimulation lead.

To position the stimulation lead, one aspect of the technique involves inserting the stimulation lead between a first vertebra and a second vertebra into an epidural space and advancing the stimulation lead in an inferior direction, substantially parallel to a longitudinal direction of the epidural space.

To position the stimulation lead, another aspect of the technique involves inserting the stimulation lead between a first vertebra and a second vertebra into an epidural space and advancing the stimulation lead in an inferior direction, wherein the stimulation lead laterally and/or obliquely transverses the epidural space.

To position the stimulation lead, yet another aspect of the technique involves inserting the stimulation lead into an epidural space at or superior to a desired vertebral placement position.

An object of the present invention is to electrically stimulate physically-selected (or anatomically-selected) spinal nerve roots within the epidural space of a patient to at least inhibit the transmission of pain signals from a pain-afflicted region of the body to the brain of a patient.

Another object of the present invention is to electrically stimulate physically-selected (or anatomically-selected) spinal nerve roots within the epidural space of a patient to facilitate control of symptoms of motor/muscular disorders.

Another object of the present invention is to provide a method for inserting a stimulation lead in an inferior direction relative to a vertebral column.

Another object of the present invention is to provide a method for inserting a stimulation lead in a trans-spinal direction.

Another object of the present invention is to provide a method for inserting and ultimately positioning at least one stimulation lead so that an electrode portion of the stimulation lead is in a plane substantially parallel to selected spinal nerve roots at a position within the epidural space, at spinal ganglion, at a neural plexus, and/or at a peripheral portion thereof.

Other objects and advantages of the present invention will be apparent to those of ordinary skill in the art having reference to the following specification together with the drawings.

BRIEF DESCRIPTION OF THE DRAWINGS

FIG. 1b is a partial plan view illustrating the insertion technique of FIG. 1a;

FIG. 2b is a partial, cross-sectional view taken along line II—II in FIG. 2a;

DETAILED DESCRIPTION OF THE PREFERRED EMBODIMENTS

In accordance with the present invention, a placed stimulation lead enters an epidural space of a patient at a vertebral position at or superior to a distal end of the positioned stimulation lead. The distal end of the positioned stimulation lead, or the electrode portion of the lead, is positioned in a plane parallel to selected spinal nervous tissue.

In a preferred embodiment, the stimulation lead is a percutaneously inserted, multiple electrode lead which is entered into the epidural space through a Touhy-like needle (hereinafter, an "insertion needle") positioned between selected vertebrae. Specifically, an insertion needle is passed between selected vertebrae; whereas, the distal end of the insertion needle is positioned within the epidural space. One or more stimulation leads are passed through the bore of the needle and guided in an inferior or laterally and/or obliquely transverse direction to a desired vertebral level.

While the stimulation lead may be finally positioned within the epidural space, guiding the stimulation lead in an inferior direction allows at least the electrode portion of the lead to be passed through an intervertebral foramen and to follow selected spinal nervous tissue. In other words, an implanting user is able to anatomically, or physically, select specific spinal nervous tissue for stimulation. Of note, inferior-to-superior insertion of a stimulation lead does not typically facilitate a distal tip of a stimulation lead to exit an intervertebral foramen.

Figure 3:
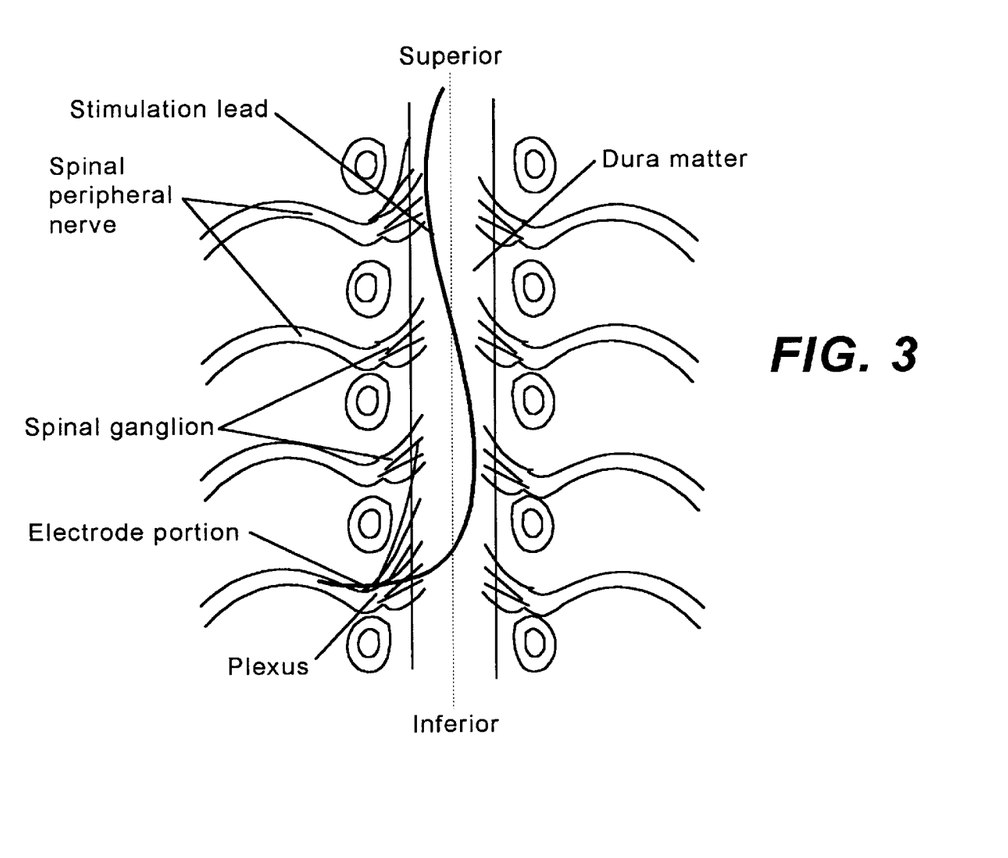
FIG. 3 is a partial, plan view showing stimulation lead placement in accordance with one aspect of the present invention.

The distance between the distal tip of a stimulation lead and the foramen in which the stimulation lead passes dictates the scope of neural influence which may be achieved through stimulation. In general, spinal nervous tissue (for example, a nerve root) progresses from that within the epidural space to spinal ganglia, which exits the vertebral column, to a nerve plexus outside the vertebral column and, finally, to a more distal peripheral portion of the nerve. Accordingly, a stimulation lead may be passed through an intervertebral foramen and its final position will span all or some portion of the regions of the spinal nervous tissue (FIG. 3); provided however, the stimulation lead includes an adequate number of electrodes (for example, four or eight electrodes). Importantly, as the spinal nervous tissue is physically selected, a user is not required to expend a significant level of energy to isolate the desired spinal nervous tissue through defining the electrical energy.

Figure 4:
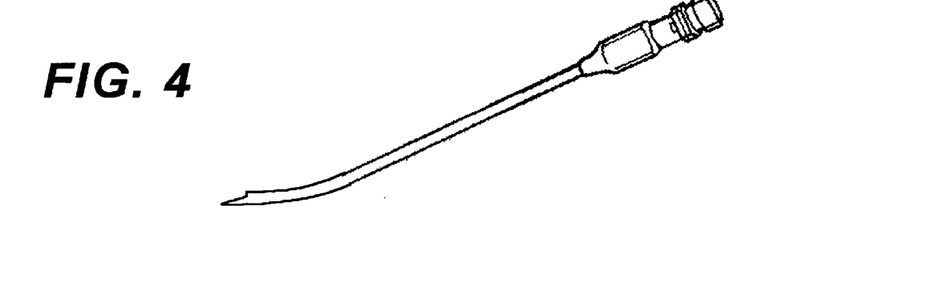
FIG. 4 is a curved insertion needle for practicing an insertion method in accordance with the present invention.
Figure 5:
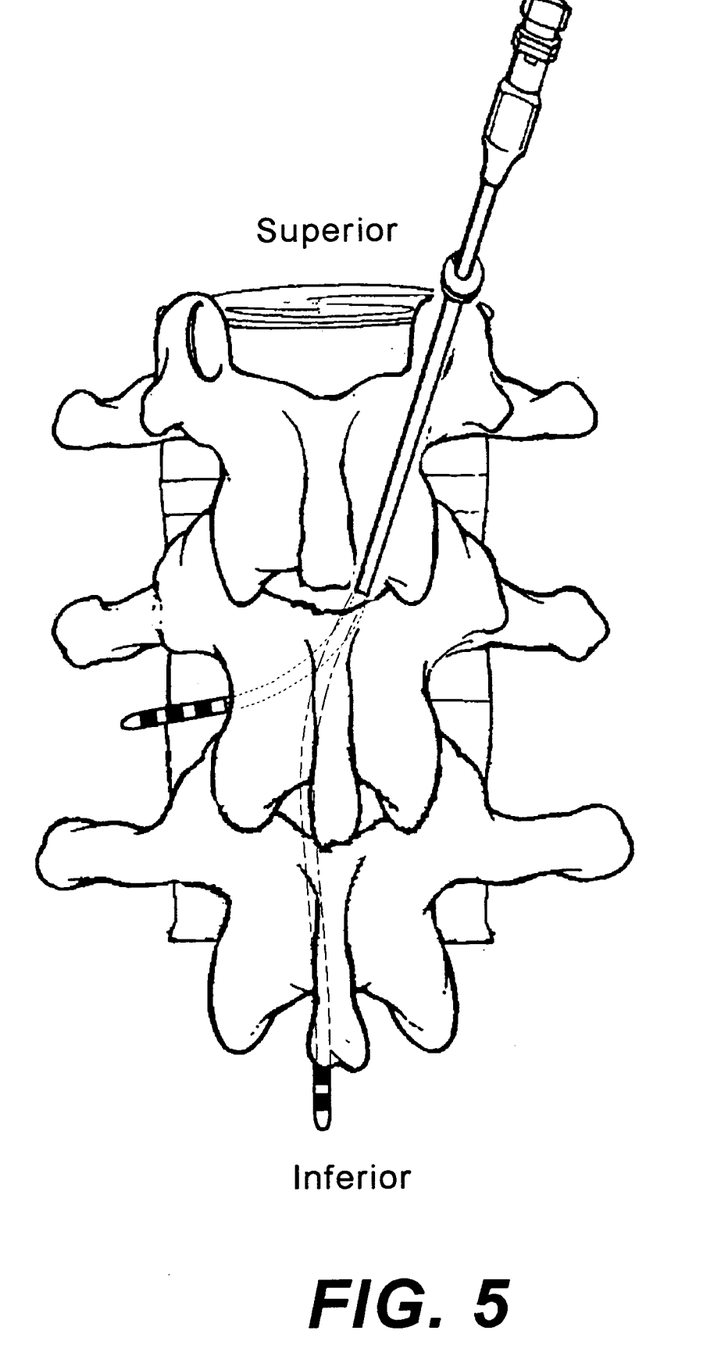
FIG. 5 is a partial, plan view showing stimulation lead placement in accordance with another aspect of the present invention.

As a first approach and in reference to FIG. 5, using a conventional insertion needle and a non-steerable stimulation lead, a stimulation lead may be inserted into the epidural space in a superior position and directed inferiorly to an intervertebral foramen within a lumbosacral region (T12/L1 to S4/S5). Utilizing a curved needle (FIG. 4) and/or a stimulation lead which is steerable (not shown), a stimulation lead may be inserted into the epidural space in a superior position and directed inferiorly to an intervertebral foramen within a cervical region (C1/C2 to C3/C4); a cervicobrachial region (C4/C5 to C8/T1); thoracic region (T1/T2 to T11/T12); or a lumbosacral region (T12/L1 to S4/S5).

Figure 6:
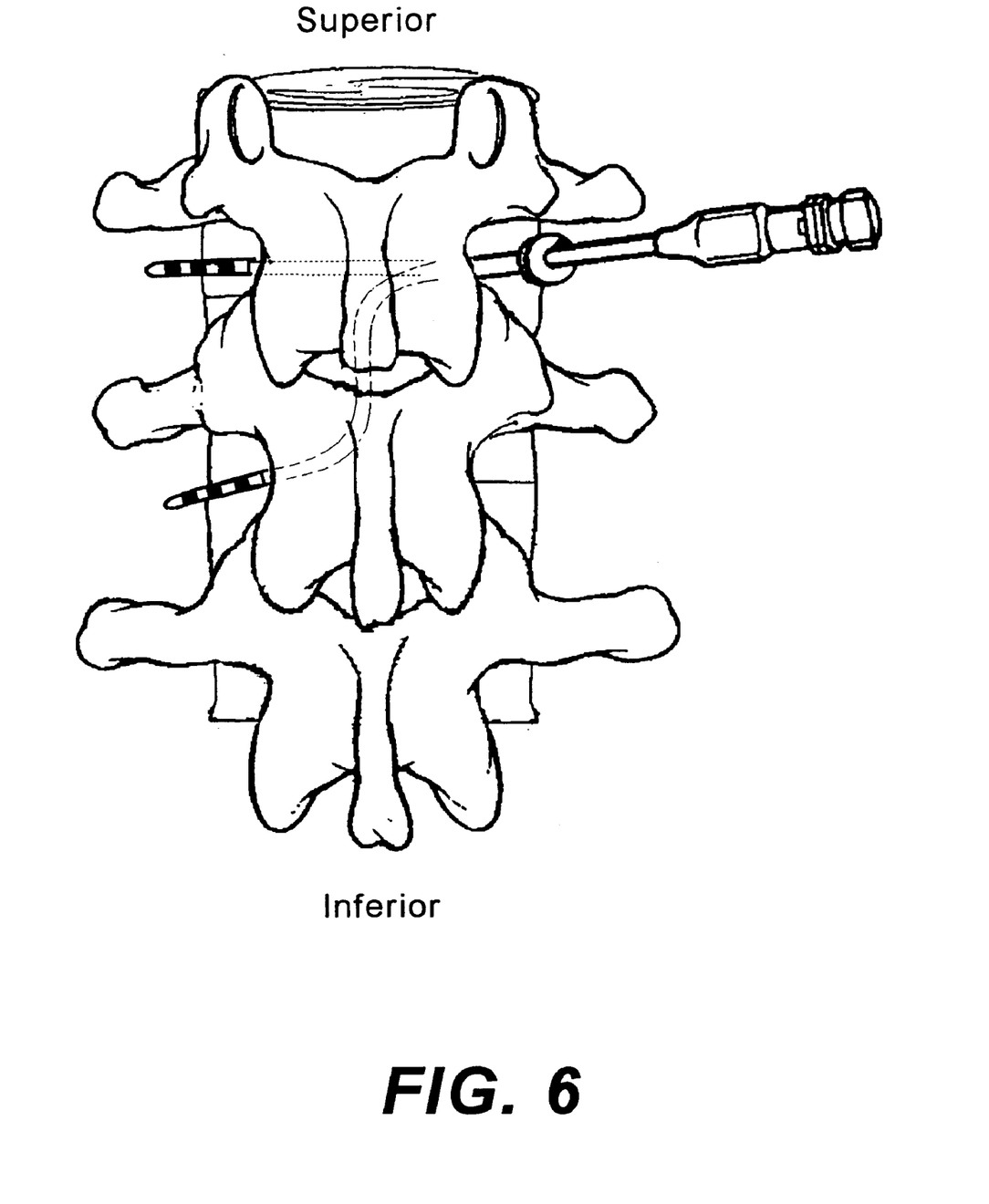
FIG. 6 is a partial, plan view showing stimulation lead placement in accordance with yet another aspect of the present invention.

As a second approach, due to the exit angle of spinal nervous tissue from the spinal cord (approximately 90°), an insertion technique in accordance with the above description, without a stimulation lead capable of achieving significant steering angles, may not be capable of placing a distal end of a stimulation lead through a desired intervertebral foramen. Accordingly, a stimulation lead may be inserted so as to laterally and/or obliquely transverse the epidural space between an insertion point and a final placement position, where the final placement position may require passage of the stimulation lead through an intervertebral foramen (see FIG. 6). For this approach, a stimulation lead insertion point may be at the same vertebra from which the stimulation lead exits.

The implantation technique for transversing an epidural space with a stimulation lead, or trans-spinal insertion, may be used to place stimulation leads in a cervical region, a cervicobrachial region, a thoracic region, a lumbar region, and a sacral region.

The percutaneous leads are coupled to one or more conventional neurostimulation devices, or signal generators. The devices can be totally implanted systems and/or radio frequency (RF) systems. An example of an RF system is a MNT/MNR-916CC system manufactured by Advanced Neuromodulation Systems, Inc. of Allen, Tex.

The preferred neurostimulation devices should allow each electrode of each lead to be defined as a positive, a negative, or a neutral polarity. For each electrode combination (i.e, the defined polarity of at least two electrodes having at least one cathode and at least one anode), an electrical signal can have at least a definable amplitude (i.e, voltage), pulse width, and frequency, where these variables may be independently adjusted to finely select the sensory transmitting nerve tissue required to inhibit transmission of pain signals and/or motor-related nerve tissue required to control motor signals associated with motor disorders or the like. Generally, amplitudes, pulse widths, and frequencies are determinable by the capabilities of the neurostimulation systems and are not critical to the present invention other than to enable pain management/motor control.

While the invention has been described herein relative to a number of particularized embodiments, it is understood that modifications of, and alternatives to, these embodiments, such modifications and alternatives realizing the advantages and benefits of this invention, will be apparent those of ordinary skill in the art having reference to this specification and its drawings. It is contemplated that such modifications and alternatives are within the scope of this invention as subsequently claimed herein, and it is intended that the scope of this invention claimed herein be limited only by the broadest interpretation of the appended claims to which the inventors are legally entitled.

What is claimed is:

1. A method of administering particularized electrical energy to spinal nervous tissue using a signal generator and at least one stimulation lead having an electrode portion and a connector portion, where the connector portion may be electrically coupled to the signal generator, the method comprising the steps of:

inserting the at least one stimulation lead between a first vertebra and a second vertebra and into an epidural space and advancing the stimulation lead in an inferior direction, substantially parallel to a longitudinal direction of the epidural space;

positioning the stimulation lead so that the electrode portion of the stimulation lead lies in a plane substantially parallel to selected spinal nervous tissue, the selected spinal nervous tissue including at least one of: epidural spinal nervous tissue, spinal ganglion, neural plexus, and peripheral nerves;

coupling the at least one stimulation lead to the signal generator; and delivering electrical energy from the signal generator to the electrode portion of the at least one stimulation lead.

2. A method in accordance with claim 1, wherein a distal end of the stimulation lead is positioned with a cervical region, wherein the distal end of the stimulation lead is at or between a C1, C2, C3, or C4 vertebral position.

3. A method in accordance with claim 1, wherein a distal end of the stimulation lead is positioned with a cervicobrachial region, wherein the distal end of the stimulation lead is at or between a C5, C6, or C7, vertebral position.

4. A method in accordance with claim 1, wherein a distal end of the stimulation lead is positioned with a thoracic region, wherein the distal end of the stimulation lead is at or between a T1, T2, T3, T4, T5, T6, T7, T8, T9, T10, T11, or T12 vertebral position.

5. A method in accordance with claim 1, wherein a distal end of the stimulation lead is positioned with a lumbar region, wherein the distal end of the stimulation lead is at or between an L1, L2, L3, L4, or L5 vetebral position.

6. A method in accordance with claim 1, wherein a distal end of the stimulation lead is positioned within a sacral region, wherein the distal end of the stimulation lead is at or between S1, S2, S3, S4, or S5.

7. A method in accordance with claim 1, wherein the stimulation lead extends, at least in part, through an intervertebral foramen.

8. A method in accordance with claim 1, wherein delivered electrical energy inhibits transmission of sensory signals within the selected spinal nervous tissue.

9. A method in accordance with claim 1, wherein delivered electrical energy affects transmission of motor signals within the selected spinal nervous tissue.

10. A method in accordance with claim 1, wherein delivered electrical energy affects transmission of sensory signals within the selected spinal nervous tissue.

11. A method in accordance with claim 1, wherein delivered electrical energy inhibits transmission of motor signals within the selected spinal nervous tissue.

12. A method of administering particularized electrical energy to spinal nervous tissue using a signal generator and at least one stimulation lead having an electrode portion and a connector portion, where the connector portion may be electrically coupled to the signal generator, the method comprising the steps of:
   inserting the at least one stimulation lead between a first vertebra and a second vertebra and into an epidural space and advancing the stimulation lead in an inferior direction, wherein the stimulation lead transverses, whether obliquely or laterally, the epidural space;
   positioning the stimulation lead so that the electrode portion of the stimulation lead lies in a plane substantially parallel to selected spinal nervous tissue, the selected spinal nervous tissue including at least one of: epidural spinal nervous tissue, spinal ganglion, nerve plexus, and peripheral nerves;
   coupling the at least one stimulation lead to the signal generator; and
   delivering electrical energy from the signal generator to the electrode portion of the at least one stimulation lead.

13. A method in accordance with claim 12, wherein a plurality of stimulation leads are implanted and coupled to at least one signal generator.

14. A method in accordance with claim 12, wherein a distal end of the stimulation lead is positioned with a cervical region, wherein the distal end of the stimulation lead is at or between a C1, C2, C3, or C4 vertebral position.

15. A method in accordance with claim 12, wherein a distal end of the stimulation lead is positioned with a cervicobrachial region, wherein the distal end of the stimulation lead is at or between a C5, C6, or C7 vertebral position.

16. A method in accordance with claim 12, wherein a distal end of the stimulation lead is positioned with a thoracic region, wherein the distal end of the stimulation lead is at or between a T1, T2, T3, T4, T5, T6, T7, T8, T9, T10, T11, or T12 vertebral position.

17. A method in accordance with claim 12, wherein a distal end of the stimulation lead is positioned with a lumbar region, wherein the distal end of the stimulation lead is at or between an L1, L2, L3, L4, or L5 vertebral position.

18. A method in accordance with claim 12, wherein a distal end of the stimulation lead is positioned within a sacral region, wherein the distal end of the stimulation lead is at or between S1, S2, S3, S4, or S5.

19. A method in accordance with claim 12, wherein the stimulation lead extends, at least in part, through an intervertebral foramen.

20. A method in accordance with claim 12, wherein delivered electrical energy affects transmission of sensory signals within the selected spinal nervous tissue.

21. A method in accordance with claim 12, wherein delivered electrical energy affects transmission of motor signals within the selected spinal nervous tissue.

22. A method of administering particularized electrical energy to spinal nervous tissue using a signal generator and at least one stimulation lead having an electrode portion and a connector portion, where the connector portion may be electrically coupled to the signal generator, the method comprising the steps of:
   inserting the at least one stimulation lead into an epidural space at or superior to a desired vertebral placement position;
   positioning the at least one stimulation lead so that the electrode portion of the stimulation lead lies in a plane substantially parallel to selected spinal nervous tissue and is capable of directly influencing, through delivery of electrical energy, at least one of: nerve tissue within the epidural space, spinal ganglia, a nerve plexus, and a peripheral nerve;
   coupling the at least one stimulation lead to the signal generator; and
   delivering electrical energy from the signal generator to the electrode portion of the at least one stimulation lead.

23. A method in accordance with claim 22, wherein delivered electrical energy affects transmission of sensory signals within the selected spinal nervous tissue.

24. A method in accordance with claim 22, wherein delivered electrical energy affects transmission of motor signals within the selected spinal nervous tissue.

25. A method of administerin particularized electrical energy to spinal nervous tissue using a signal generator and at least one stimulation lead having an electrode portion and a connector portion, where the connector portion may be electrically coupled to the signal generator, the method comprising the steps of:
   inserting the at least one stimulation lead between a first vertebra and a second vertebra and into an epidural space and advancing the stimulation lead in an inferior direction, substantially parallel to a longitudinal direction of the epidural space;
   positioning the stimulation lead so that the electrode portion of the stimulation lead lies in a plane substantially parallel to selected spinal nervous tissue having corresponding nerve roots originating superior to an S1 vertebral position, the selected spinal nervous tissue including at least one of: epidural spinal nervous tissue, spinal ganglion, neural plexus, and peripheral nerves;
   coupling the at least one stimulation lead to the signal generator; and
   delivering electrical energy from the signal generator to the electrode portion of the at least one stimulation lead.

26. A method in accordance with claim 25, wherein a distal end of the stimulation lead is positioned within a cervical region, wherein the distal end of the stimulation lead is at or between a C1, C2, C3, or C4 vetebral position.

27. A method in accordance with claim 25, wherein a distal end of the stimulation lead is positioned within a cervicobrachial region, wherein the distal end of the stimulation lead is at or between a C5, C6, or C7 vertebral position.

28. A method in accordance with claim 25, wherein a distal end of the stimulation lead is positioned within a thoracic region, wherein the distal end of the stimulation lead is at or between a T1, T2, T3, T4, T5, T6, T7, T8, T9, T10, T11, or T12 vertebral positiion.

29. A method in accordance with claim 25, wherein a distall end of the stimulation lead is positioned within a lumbar region, wherein the distal end of the stimulation lead is at or between an L1, L2, L3, L4, or L5 vertebral position.

30. A method in accordance with claim 25, wherein a distal end of the stimulation lead is positioned at or inferior to an S1 vertebral position.

31. A method in accordance with claim 25, wherein the stimulation lead extends, at least in part, through an intervertebral foramen.

32. A method in accordance with claim 25, wherein delivered electrical energy inhibits transmission of sensory signals within the selected spinal nervous tissue.

33. A method in accordance with claim 25, wherein delivered electrical energy affects transmission of motor signals within the selected spinal nervous tissue.

34. A method in accordance with claim 25, wherein delivered electrical energy affects transmission of sensory signals within the selectred spinal nervous tissue.

35. A method in accordance with claim 25, wherein delivered electrical energy inhibits transmission of motor signals within the selected spinal nervous tissue.

36. A method in accordance with claim 25, wherein a distal end of the stimulation lead is placed at an intraspinal position.

37. A method of administering particularized electrical energy to spinal nervous tissue using a signal generator and at least on stimulation lead having an electrode portion and a connector portion, where the connector portion may be electrically coupled to the signal generator, the method comprising the steps of:

inserting the at least one stimulation lead into an epidural space at or superior to a desired bertebral plaement position;

positioning the at least one stimulation lead so that the electrode portion of the stimulation lead (i) lies in a plane substantially parallel to selected spinal nervous tissue having corresponding nerve roots originating superior to an S1 vertebral position and (ii) is capable of directly influencing, through delivery of electrical energy, at least one of: nerve tissue within the epidural space, spinal ganglia, a nerve plexus, and a peripheral nerve;

coupling the at least one stimulation lead to the signal generator; and delivering electrical energy from the signal generator to the electrode portion of the at least one stimulation lead.

38. A method in accordance with claim 37, wherein delivered electrical energy affects transmission of sensory signals within the selected spinal nervous tissue.

39. A method in accordance with claim 37, wherein delivered electrical energy affects transmission of motor signals within the selected spinal nervous tissue.

40. A method of managing effects of a motor disorder using a signal generator and at least one stimulation lead having an electrode portion and a connector portion, where the connector portion is electrically connectable to the signal generator, the method comprising the steps of:

surgically implanting the at least one stimulation lead so that the electrode portion of the at least one stimulation lead lies in a plane substantially parallel to selected sacral spinal nervous tissue within an epidural space of a sacrum;

coupling the at least one stimulation lead to the signal generator; and delivering electrical energy from the signal generator to the electrode portion of the at least one stimulation lead so as to affect a transmission of motor signals within the selected sacral spinal nervous tissue for purposes of managing effects of the motor disorder, wherein a distal end of the stimulation lead is finally positioned at or between and S1, S2, S3, S4, or S5 sacral position.

41. A method of managing effects of a motor disorder using at least one signal generator and at least one stimulation lead having an electrode portion and a connector portion, where the connector portion is electrically connectable to the signal generator, the method comprising the steps of:

inserting the at least one stimulation lead at a vertebral position superior to S1/S2 into epidural space and advancing the stimulation lead in an inferior direction, substantially parallel to a longitudinal direction of the epidural space;

positioning the stimulation lead so that the electrode portion of the stimulation lead lied in a plane substantially parallel to selected sacral nerve roots within the epidural space of a sacrum;

coupling the at least one stimulation lead to the signal generator; and delivering electrical energy from the signal generator to the electrode portion of the at least one stimulation lead so as to affect a transmission of motor signals within the selected sacral nerve roots for purposes of managing effects of the motor disorder, wherein a distal end of the stimulation lead is finally positioned at or between an S1, S2, S3, S4, or S5 sacral position.

42. A method of managing effects of a motor disorder using a signal generator and at least one stimulation lead having an electrode portion and a connector portion, where the connector portion is electrically connectable to the signal generator, the method comprising the steps of:

inserting the at least one stimulation lead at a vetebral position superior to S1/S2 into an epidural space and advancing the stimulation lead in an inferior direction, substantially parallel to a longitudinal direction of the epidural space;

positioning the lead so that the electrode portion of the lead lies in a plane substantially parallel to selected sacral nerve roots and is capable of directly influencing, through delivery of electrical energy, at least one of: nerve tissue within the epidural space of a sacrum, a dorsal root ganglia of the sacrum, a sacral nerve plexus, and a peripheral nerve of a pelvic region;

coupling the at least one stimulation lead to the signal generator; and delivering electrical energy from the signal generator to the electrode portion of the at least one stimulation lead so as to affect a transmission of motor signals within the selected sacral nerve roots for purposes of managing effects of the motor disorder, wherein a distal end of the at least one stimulation lead is finally positioned at or between an S1, S2, S3, S4, or S5 sacral position.

* * * * *

UNITED STATES PATENT AND TRADEMARK OFFICE
CERTIFICATE OF CORRECTION

PATENT NO. : 6,104,957
DATED : August 15, 2000
INVENTOR(S) : Kenneth M. Alo et al.

It is certified that error appears in the above-identified patent and that said Letters Patent is hereby corrected as shown below:

Column 1,
Line 11, delete "10".
Line 60, delete "Allen", and insert --Plano--.

Column 5,
Line 54, delete "Allen", and insert --Plano--.

Column 6,
Line 39, delete "with", and insert --within--.
Line 43, delete "with", and insert --within--.
Line 45, after "C7", delete ",".
Line 47, delete "with", and insert --within--.
Line 54, delete "with", and insert --within--.

Column 7,
Line 32, delete "with", and insert --within--.
Line 36, delete "with", and insert --within--.
Line 41, delete "with", and insert --within--.
Line 46, delete "with", and insert --within--.

Column 8,
Line 21, delete "administerin", and insert --administering--.
Line 57, delete "positiion" and insert --position--.
Line 59, delete "distall", and insert --distal--.

Column 9,
Line 9, delete "selectred", and insert --selected--.
Line 18, delete "on", and insert --one--.
Line 23, delete "bertebral plaement", and insert --vertebral placement--.

UNITED STATES PATENT AND TRADEMARK OFFICE
CERTIFICATE OF CORRECTION

PATENT NO. : 6,104,957
DATED : August 15, 2000
INVENTOR(S) : Kenneth M. Alo et al.

It is certified that error appears in the above-identified patent and that said Letters Patent is hereby corrected as shown below:

<u>Column 10,</u>
Line 4, delete "and", and insert --an--.
Line 13, between "into" and "epidural", insert --an--.
Line 18, delete "lied", and insert --lies--.

Signed and Sealed this

Seventh Day of August, 2001

Attest:

Attesting Officer

NICHOLAS P. GODICI
*Acting Director of the United States Patent and Trademark Office*